United States Patent [19]

Wieder

[11] Patent Number: 4,810,193

[45] Date of Patent: Mar. 7, 1989

[54] TOOTH SHADE GUIDE CASTING FORM

[76] Inventor: Steven M. Wieder, 126 Avenida Veneccia, Sarasota, Fla. 34242

[21] Appl. No.: 129,581

[22] Filed: Dec. 7, 1987

Related U.S. Application Data

[63] Continuation-in-part of Ser. No. 041,463, Apr. 23, 1987, abandoned.

[51] Int. Cl.⁴ .............................................. A61C 19/10
[52] U.S. Cl. ......................................... 433/26; 433/34
[58] Field of Search ............................. 433/26, 34, 40

[56] References Cited

U.S. PATENT DOCUMENTS

| 785,992 | 3/1905 | Whiteley | 433/26 |
|---|---|---|---|
| 1,327,306 | 1/1920 | Berger | 433/26 |
| 1,518,608 | 12/1924 | Short | 433/26 |
| 2,249,634 | 7/1941 | Myerson | 433/26 |
| 2,479,543 | 8/1949 | Russell | 433/26 |
| 4,115,922 | 9/1978 | Alderman | 433/26 |
| 4,382,784 | 5/1983 | Freller | 433/26 |
| 4,541,801 | 9/1985 | Mackert et al. | 433/26 |
| 4,618,325 | 10/1986 | Appelle | 433/26 |

FOREIGN PATENT DOCUMENTS 169093 10/1951 Austria .................. 433/26

Primary Examiner—John J. Wilson
Attorney, Agent, or Firm—Charles J. Prescott

[57] ABSTRACT

A tooth shade guide casting form for in-office preparation of shade samples of tooth color restoration material (TCRM) to be utilized by dentists in the restoration of a patient's tooth surface. The invention includes a handle, preferably of thin transparent plastic, and a detachable bowl disposed from one end of the handle. The bowl is preferrably the size and shape of a human tooth and is adapted to receive a quantity of photocurable TCRM to be hardened therein. After hardening, the bowl is detached from the handle, leaving the cured TCRM shade sample attached to the first end of the handle. Such samples, having the contour of the bowl, are then used by dentists in selecting the properly colored TCRM for restoring patients' teeth. The handle may also include means disposed at its other end for retaining and displaying a label designating the particular TCRM, while the invention may also include a separate holder for retaining and displaying a plurality of handles with TCRM shade samples attached for easier color selection prior to selection and repair.

14 Claims, 2 Drawing Sheets

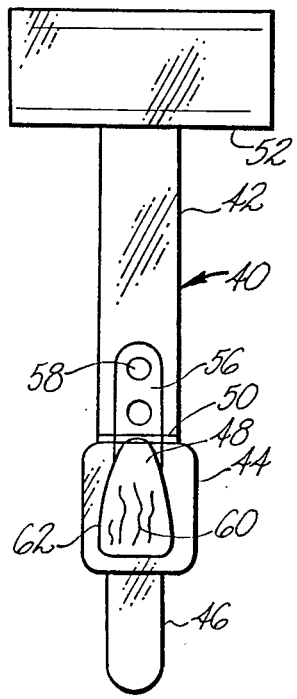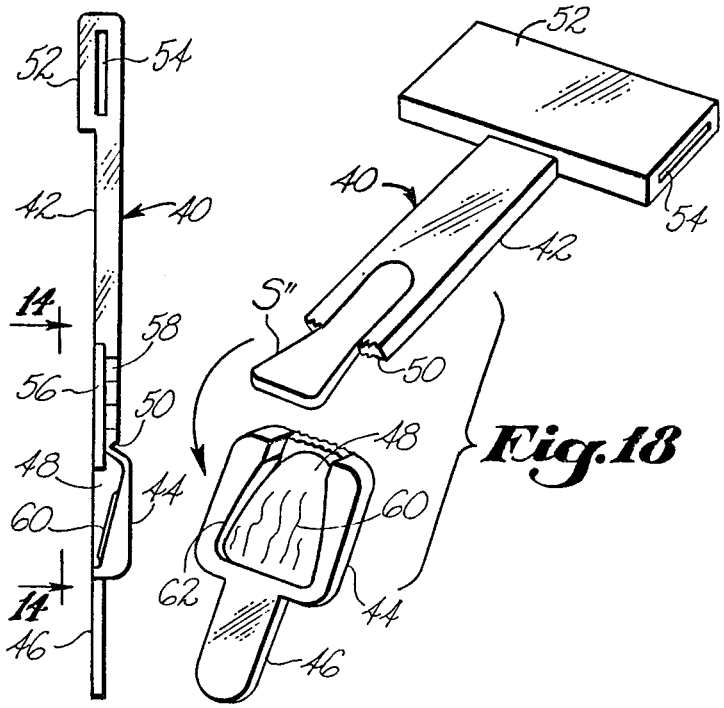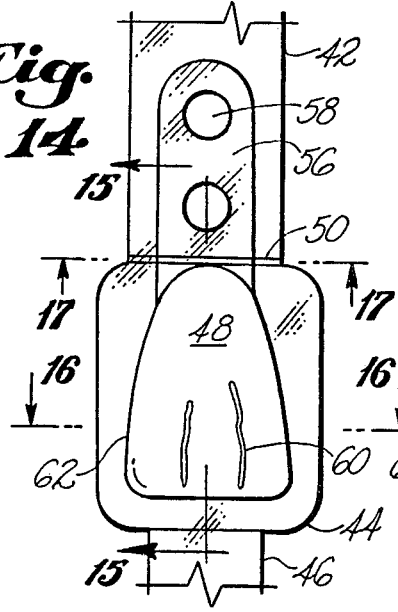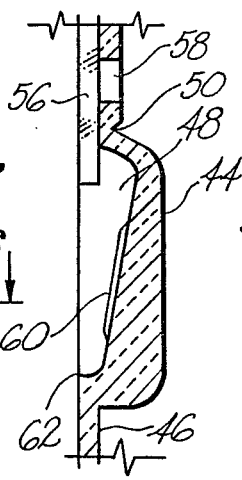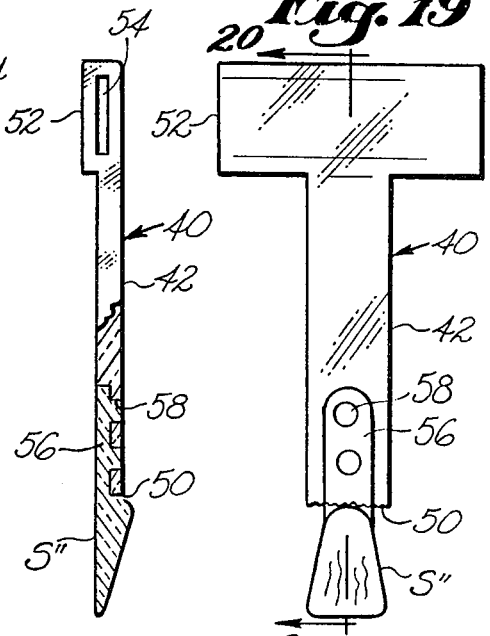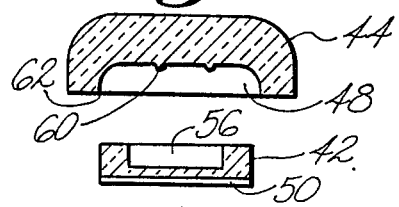

TOOTH SHADE GUIDE CASTING FORM

BACKGROUND OF THE INVENTION

This application is a continuation-in-part of application Ser. No. 07/041,463 filed On Apr. 23, 1987, now abandoned.

This invention relates generally to devices for assisting dentists in the restoration of patients' teeth, and more particularly to a device adapted to allow dentists to prepare their own tooth color restorative material (TCRM) shade samples in office.

For some time now, dentists have had the facility to restore the exposed surfaces of patients' teeth with material which quite accurately duplicates each patient's enamel so as to present a repair which visually blends with the rest of the patient's natural teeth. The restorative material is generally a photocurable or hardenable material known as tooth color restorative material (TCRM) in the profession.

The uncured TCRM paste, once selected, is applied to a patient's tooth surface, after which an appropriate light source is shown thereon to cure and harden the TCRM in a very short time period. Where required thereafter, the dentist may further shape the cured TCRM applied to the repaired surface contour to better blend it with the other teeth.

One of the major drawbacks to such repair resides in the accurate selection of the color or shade of the TCRM. A number of suppliers provide TCRM in a broad variety of shades for selection by the dentist. Accompanying each TCRM repair kit is typically a color sample which includes a plurality of plastic pieces each having a shape similar to a human tooth and each having a different shade which is intended to represent the color of each particular TCRM by code or name designation.

In practice, however, the majority, if not all of the associated samples provided by the manufacturers of each TCRM do not accurately reflect the true shade of the TCRM which correlates with the sample provided. Further, in most, if not all cases, the shade samples provided by the manufacturers are fabricated or molded of a plastic material which is not identical in content or in consistency to the TCRM itself.

In any event, the dentist utilizing the TCRM is at a serious disadvantage when attempting to select a TCRM which identically matches a particular patient's tooth or teeth to be repaired. The best that the dentist now may do is to compare the samples provided with the coloration of the patient's teeth and then make the selection accordingly. However, applicant, as a dentist, has repeatedly found inconsistencies in coloration between the samples provided and the actual TCRM and, as a result, the finished dental product typically does not identically match the rest of the patient's original teeth.

A further problem resides in the overall limitation of the variety of shades of TCRMs presently available. Applicant has found that blending two or more TCRMs may produce a closer coloration match with a particular patient's teeth.

One such standardized system of color and shade selection for TCRMs is disclosed in U.S. Pat. No. 4,115,922 to Alderman which holds removable shade guide selectors each of which have a distinct variation and thickness intended to aid in the more accurate selection of the particular TCRM. However, this invention is not intended for use in the actual preparation of a customized shade guide with blended TCRM.

Disclosed in U.S. Pat. No. 4,618,325 to Appelle is the only reference known to applicant which teaches a custom dental shade guide form intended for the actual cast forming of individual shade guides from an individual and customized blend of TCRMs. However, in one embodiment of this invention, the mold blank is separate and must be filled and retained manually in place so that a button 23 disposed at one end of an elongated handle remains embedded within the TCRM as it is cured. In the other embodiment, the mold blank is connected in side-by-side fashion to the end of the handle adjacent the button and constructed such that, after the uncured TCRM is deposited into and fills the mold blank, the blank and contents must be doubled back against the handle end and held such that the button remains embedded within the TCRM during curing. Further, all embodiments of the mold blank have overlapping play view projections with respect to the cavity whose side contours inwardly extends to form the peripheral lip 28 and opening 29. Such a structure makes removal of the mold blank from the harded TCRM extremely difficult at best.

Further, only the '325 patent to Appelle is known to applicant which allows the dental practitioner to prepare or have available TCRM shade samples which reasonably reflect the coloration of a particular shade sample or allow accurate blending of two or more TCRMs to achieve reasonable shade matching. However, even the Appelle reference disposes the shade sample itself in front of a significant portion of the handle including the button embedded in the shade sample and the associated handle therebehind so as to potentially interfere with the careful color and subtle shade comparison with a patient's real teeth to be repaired.

The present invention provides a casting form and associated holder which allows the dental practitioner to prepare any number of TCRM samples by utilizing each manufacturer's TCRM supplied and to thereafter prepare cured and hardened color samples fabricated of the actual TCRM or combination of TCRMs which will be put to use by the dental practitioner. Further, the present invention is easy and simple to use in a dental office setting and also may provide samples which include surface features which are similar to an actual tooth to enhance the color comparison and selection process.

BRIEF SUMMARY OF THE INVENTION

The present invention is directed to a tooth shade guide casting form for in-office preparation of shade samples of tooth color restoration material (TCRM) to be utilized by dentists in the restoration of a patient's tooth surface. The invention includes a handle, preferably of thin transparent plastic, and a detachable bowl disposed from one end of the handle. The bowl is preferably the size and shape of a human tooth and is adapted to receive a quantity of photocurable TCRM to be hardened therein. After hardening, the bowl is detachable from the handle, leaving the cured TCRM shade sample attached to the first end of the handle. Such samples having the contour of the bowl, are then used by dentists in selecting the properly colored TCRM for restoring patients' teeth. The handle may also include means disposed at its other end for retaining and displaying a label designating the particular TCRM, while the invention may further include a separate holder for retaining and displaying a plurality of handles with TCRM shade samples attached for easier color selection prior to selection and repair.

It is therefore an object of this invention to provide a tooth shade and color guide casting form for facilitating in-office preparation of TCRM shade samples for use in the accurate color selection of a particular TCRM for use by a dental practioner or trained staff in repairing teeth.

It is another object of the present invention to provide a holder for retaining a selection of TCRM shade samples for quick and easy color comparison and selection prior to actual tooth repair.

It is yet another object to provide the above invention which is economical to manufacture and simple and convenient for the dental practitioner or trained staff to utilize in preparing TCRM shade samples.

It is yet another object of the above invention to also provide means for retaining labels in conjunction with each prepared sample so as to identify the particular manufacturer and product identification number associated with each prepared TCRM shade sample.

It is yet another object of the above invention to facilitate accurate and repeatable in-office preparation of TCRM shade samples which are a blend of two or more TCRMs.

In accordance with these and other objects which will become apparent hereinafter, the instant invention will now be described with reference to the accompanying drawings in which:

BRIEF DESCRIPTION OF THE DRAWINGS

FIG. 12 is a front elevation view of the prefered embodiment of the invention.

FIG. 13 is a side elevation view of the invention as shown in FIG. 12.

FIG. 14 is an enlarged view in the direction of arrows 14—14 in FIG. 13.

FIG. 15 is a section view in the direction of arrows 15—15 in FIG. 14.

FIG. 16 is a section view in the direction of arrows 16—16 in FIG. 14.

FIG. 17 is a section view in the direction of arrows 17—17 in FIG. 14.

FIG. 18 is a perspective view of the preferred embodiment of the invention shown in FIG. 12 ready for use after the cavity is detached therefrom.

FIG. 19 is a front elevation view of FIG. 18 absent the detached cavity.

FIG. 20 is a section view in the direction of arrows 20—20 in FIG. 19.

DETAILED DESCRIPTION OF THE INVENTION

Figure 1:
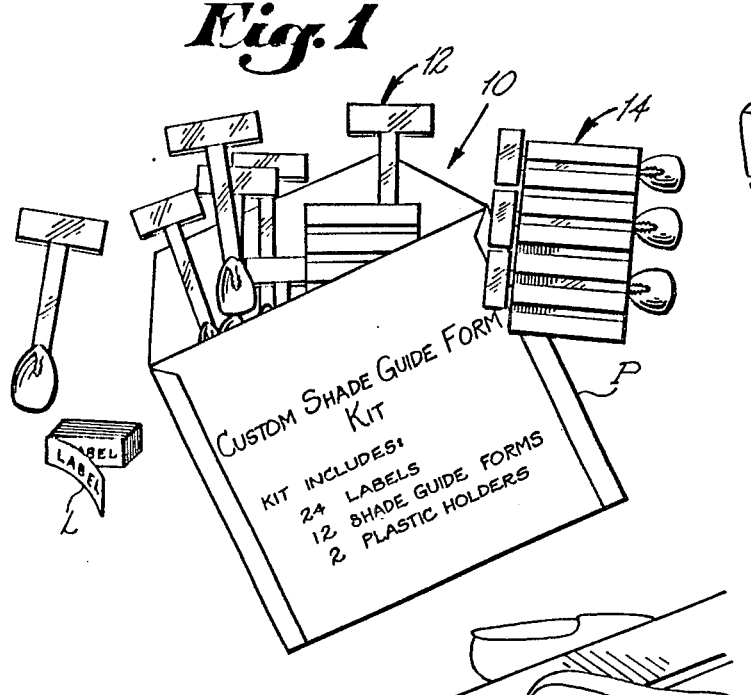
FIG. 1 is a pictorial view of one embodiment of the invention as applicant envisions same to be distributed in kit form.
Figures 2, 3:
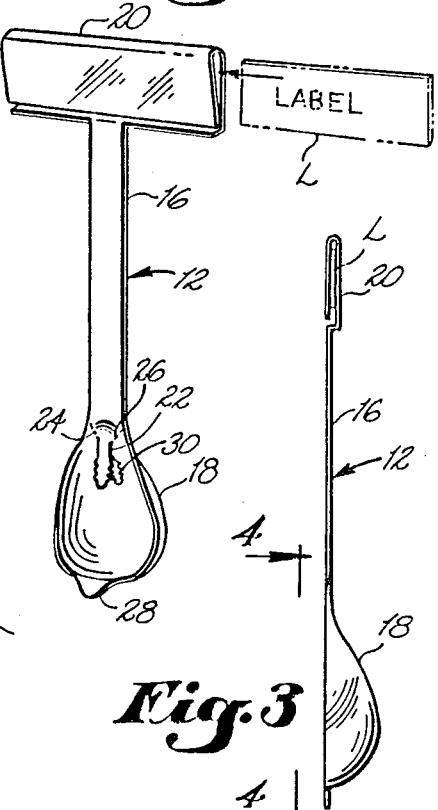
FIG. 2 is a perspective view of one embodiment of the invention.
FIG. 3 is a right side elevation view of FIG. 2.

Referring now to the drawings, and particularly to FIGS. 1, 2 and 3, the kit embodying concepts of the invention is shown generally at numeral 10 and includes a plurality of tooth shade guide casting forms 12 and a holder therefor at numeral 14 packaged within a kit package P. Each casting form 12 includes elongated handle 16 which is preferably formed of thin transparent plastic material having a bowl 18 disposed at one end. Disposed at the other end of handle 16 is a label container 20, also formed of transparent material into which label L may be inserted.

Figure 4:
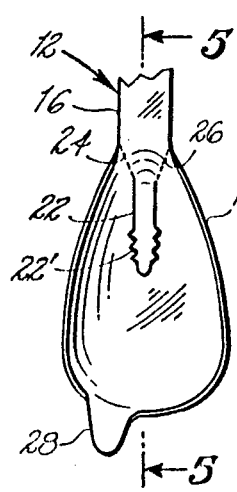
FIG. 4 is a view in the direction of arrows 4—4 in FIG. 3.
Figures 5, 8:
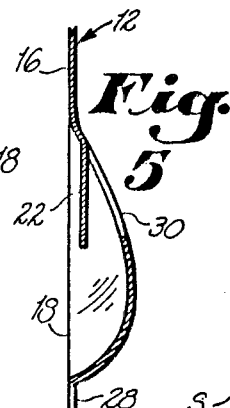
FIG. 5 is a section view in the direction of arrows 5—5 in FIG. 4.
FIG. 8 is a view similar to FIG. 5 after the TCRM color sample has been cured and hardened depicting the removal of the bowl from the cured TCRM color sample.

Referring also now to FIGS. 4 and 5, the bowl 18, in the preferred embodiment formed integral with the handle 16 and label container 20 and also formed of transparent plastic, includes prong 22 having barbs 22' thereon, the purpose of which will be described herebelow. For enhanced productivity, therefore, the casting form 12 is formed of a single sheet of thin, transparent material whereby the prong 22, disposed away inwardly into the concavity of the bowl 18, leaves a small aperture 30 in the bowl 18. The bowl 18 is separated or demarcated from the handle 16 by lines of weakness 24 and 26 and also has disposed at its lower margin a tang 28 which purposes will also be described herebelow.

Figures 6, 7:
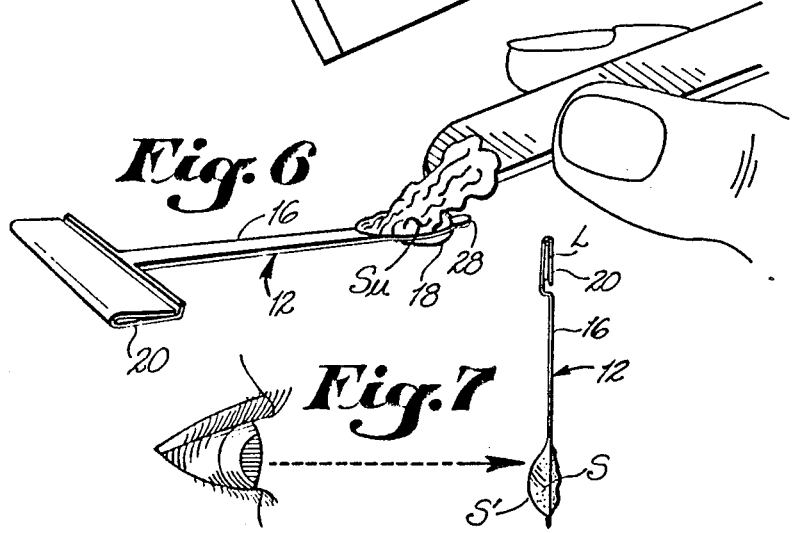
FIG. 6 is a perspective view of the invention during preparation of a TCRM color sample.
FIG. 7 is a side elevation view of a TCRM color sample prepared in accordance with the present invention in use during visual comparison.

Referring now to FIGS. 6, 7 and 8, the casting form 12 is shown in use. A portion of uncured tooth color restorative material (TCRM) in paste form shown generally at Su, is placed into the bowl 18 by a suitable applicator after the material has been mixed. A light source is then shown onto the material Su to effect curing and hardening in a short period of time. Thereafter, as best seen in FIG. 8, the tang 28 is grasped by the user's fingernail and disposed outwardly in the direction of the arrow, leaving the cured TCRM shade sample S behind molded and attached around the prong 22 and barbs 22', and thus, rigidly attached to handle 16.

As the bowl 18 is forced away from the cured sample S, fracturing occurs along the lines of weakness 24 and 26, thus breaking the bowl 18 free from handle 16 to be disposed of thereafter. The dental technician is then able to grasp the handle 16 and hold it up to a suitable light source to observe the shade of the cast surface S' of the sample S for color and shade comparison with a patient's teeth. Further, to identify the particular TCRM which has been cast into the sample S, a label L may be marked to identify the source and product identification of the uncured TCRM for future reference.

Figure 9:
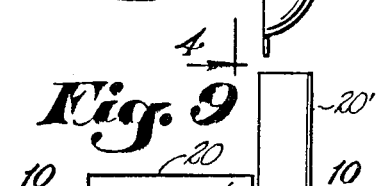
FIG. 9 is a top plan view of the invention in conjunction with a holder also provided.
Figure 11:
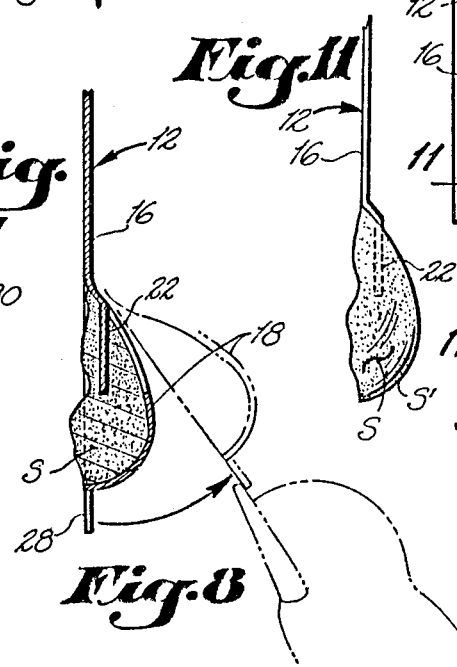
FIG. 11 is a view in the direction of arrows 11—11 in FIG. 9
Figure 10:
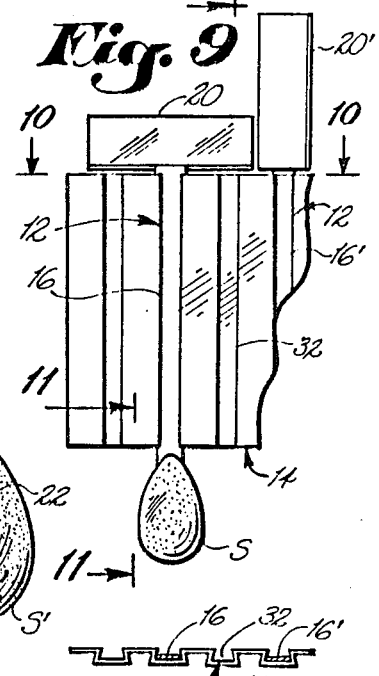
FIG. 10 is a section view in the direction of arrows 10—10 in FIG. 9.

Referring lastly to FIGS. 9, 10 and 11, a holder 14 is also provided which includes a plurality of spaced grooves 32 each for receiving and retaining a casting form 12 by receiving the handle 16 or 16' into the grooves 32 provided. Also shown in FIG. 9 is an alternate positioning of the label container 20' which is generally in alignment with, rather than transverse to, the handle 16' to facilitate closer nesting of the casting forms 12' one to another in the holder 14.

Again, referring to FIG. 11, the cured and hardened sample S is thus rigidly and permanently attached to and around prong 22 and the end of handle 16 such that the user may view surface S' for color comparison of the cured TCRM in the particular sample S to the color and shading of a patient's tooth to be repaired.

Although the bowl 18 is shown in the drawings to have a uniform surface for casting the uncured TCRM, alternately, and preferably, the bowl 18 would have the irregular contour of a tooth to be repaired. This irregular cast tooth contour would thus have the additional benefit that, in comparing the color of the sample S as in FIG. 7 adjacent a patient's teeth, a better color match-up will be facilitated as the incident light reflecting off of the sample surface S' will be similar to that reflecting off of the patient's teeth. This, to reiterate, is the primary purpose of the invention, to wit, to provide the dentist and dental technician with the enhanced facility to identically match the color and shading of each patient's teeth to a properly shaded TCRM.

The invention also provides the additional feature of allowing the dentist to blend and mix his own combination of uncured TCRMs, each combination selected from one of various suppliers to derive a broader spectrum of shades of repair material. The label container 20, having a marked label L therein, then allows the dentist to exactly blend the same proportions of TCRMs at any future date without further undue experimentation or inexactness.

Referring now to FIGS. 12 to 20, the preferred embodiment of the invention is shown generally at 40 molded generally of transparent rigid plastic and having an elongated handle 42 and a mold 44 disposed at the first end of handle 42. The mold 44, separable from handle 42 along groove or line of weakness 50, includes a main cavity portion 48 and a cavity extension 56 thereof which extends into handle 42 as will be described herebelow. Disposed from the second end of handle 42 is transversely oriented, integrally molded label container 52 having molded slot 54 formed therethrough for receiving labels L as previously described.

Referring in more detail to the structure of mold 44, cavity 48 is generally in the form of a tooth to be repaired having ridges 60 which will form striations in the color sample to be cast formed from the TCRM. These formed striations are shaped generally similar to those found in teeth and are provided to enhance the color comparison process by the more accurate reflection of light therefrom.

Cavity 48 generally has bottom and side walls which outwardly extend to form rim 62. It is important to note, as best seen in FIGS. 15 and 16, that the side walls are outwardly divergent such that the rim 62 represents the largest plan view projection of the cavity 48. This feature is importantly provided to facilitate detachment of the mold 44 as will be described herebelow.

An additional important feature of cavity 48 is that it extends in overlapping fashion into the first end of handle 42 to form cavity extension 56 as may be best seen and understood in FIGS. 14, 15 and 17. This cavity extension also includes apertures 58 which pass entirely transversely through the handle 42.

In preparing a color sample with this embodiment 40, the uncured TCRM is placed into cavity 48 and cavity extension 56 and allowed to also pass into apertures 58. The uncured TCRM is then screed flat with the rim 62 and hardened by photo curing. Thereafter, mold 44, having tab 46 disposed therefrom, is displaced out of the plane of handle 42 in the direction of the arrow in FIG. 18 such that it is broken away from handle 42 along line of weakness 50. This detaching of mold 44 is facilitated by the above-described side and rim 62 divergent relationship avoiding any overlapping projections of the cavity 60 such that there is no resistance to the disengagement of mold 44 and cavity 60 from the cured color sample S''.

As best seen in FIGS. 19 and 20, the color sample S'', being disposed longitudinally extending from handle 40, is completely clear and free of any other visual obstruction for use in accurate comparison to a patient's tooth to be repaired. Additionally, because cavity extension 56 and apertures 58 have been provided as previously described in this embodiment 40, the color sample S' securely overlaps and interengages with handle 42 as shown. This feature thus automatically secures the color sample S'' to handle 42 during the one-step process of photo curing the TCRM held within cavity 60.

While the instant invention has been shown and described herein in what is conceived to be the most practical and preferred embodiment, it is recognized that departures may be made therefrom within the scope of the invention, which is therefore not to be limited to the details disclosed herein, but is to be accorded the full scope of the claims so as to embrace any and all equivalent apparatus and articles.

What is claimed is:

1. A tooth shade guide casting form for cast forming photo curable tooth color restorative material (TCRM) color samples comprising:

an elongated handle having a first and second end and including a bowl separated from said handle first end by a transverse line of weakness, said bowl extending longitudinally from said handle first end and said line of weakness;

said bowl outwardly enlarging to its margin for receiving and supporting a quantity of TCRM during its curing and hardening process;

said line of weakness for facilitating detachment therebetween after the TCRM is cured and hardened into a shade sample, said bowl, free of overlapping projections, being detachable from said handle along said line of weakness, leaving the cured and hardened TCRM color sample connected to and extending longitudinally from said handle first end for displaying the TCRM color sample unobstructed by said handle first end, said bowl having ribs forming striations in the surface of each color sample for enhanced accuracy of color sample comparison and selection.

2. A tooth shade guide casting form as set forth in claim 1, wherein:

said handle is transparent plastic.

3. A tooth shade guide casting form as set forth in claim 1, further comprising:

label retaining means disposed from the second end of said handle for receiving replacable TCRM identifying labels.

4. A tooth shade guide casting form as set forth in claim 1, further comprising:

a holder having a plurality of spaced apart grooves each adapted to receive one said handle; said holder for displaying a plurality of cured TCRM color samples each longitudinally extending from one said handle first end.

5. A tooth shade guide casting form as set forth in claim 1, wherein
said bowl is toothed shaped.

6. A tooth shade guide casting form for cast forming photo curable tooth color restorative material (TCRM) color samples comprising:
an elongated handle having a first and second end and including an integrally formed bowl fixed and extending longitudinally from said first end;
said bowl having a bottom and sides extending divergently therefrom to its margin forming a bowl rim;
said rim forming the largest plan view projection of said bowl;
said bowl for receiving a quantity of TCRM and supporting same in a fixed relation to and extending longitudinally from said handle while the TCRM cures and hardens into a color sample;
said handle first end including a prong extending longitudinally from said handle first end into said bowl to be surrounded by and to interengage with the TCRM;
said bowl, free of overlapping projections around the color sample, detachable from said handle and a color sample along a line of weakness positioned generally transversely across said handle first end;
said color sample extending from, sand viewable in unobstructed fashion with respect to, said handle.

7. A tooth shade guide casting form as set forth in claim 6, further comprising:
label retaining means disposed from said second end of said handle for receiving replaceable TCRM identifying labels.

8. A tooth shade guide casting form as set forth in claim 7, further comprising:
ridges formed in said bowl bottom which form striations into the color samples representing a tooth's irregular exposed surface.

9. A tooth shade guide casting form as set forth in claim 8, further comprising:
a tab disposed from said rim for grasping to detach said bowl from said handle.

10. A tooth shade guide casting form for case forming photo curable tooth color restorative material (TCRM) color samples comprising:
an elongated transparent handle having a first and second end and including an integrally formed mold having a cavity fixed and extending longitudinally from its first end;
said cavity having a bottom and side walls each extending divergently therefrom to form a rim;
said cavity generally having an overall size equal to a natural tooth, said rim forming the largest plan view projection of said bowl;
said cavity having a cavity extension which extends longitudinally in overlapping fashion into said handle first end;
said cavity for receiving a quantity of TCRM and supporting same in fixed relationship to and extending longitudinally from said handle while the TCRM cures and hardens into a color sample;
said cavity, free of overlapping projections around the color sample, detachable from said handle and the color sample along a line of weakness formed generally transversely into and across said handle first end;
said color sample extending from, and viewable in unobstructed fashion with respect to, said handle.

11. A tooth shade guide casting form as set forth in claim 10, further comprising:
label retaining means disposed from said second end of said handle for receiving replaceable TCRM identifying labels.

12. A tooth shade guide casting form as set forth in claim 11, further comprising:
ridges formed in said cavity bottom which form serations into the color samples representing a tooth's irregular exposed surface.

13. A tooth shade guide casting form as set forth in claim 12, further comprising:
a tab disposed from said rim for grasping to detach said cavity from said handle.

14. A tooth shade guide casting form as set forth in claim 13, wherein:
said cavity extension includes at least one aperture through said handle such that a portion of the TCRM fills said at least one aperture, completely transecting said handle with TCRM through said at least one aperture for added strength and interengagement between said handle and the color sample.

* * * * *